United States Patent [19]

Bartfai et al.

[11] Patent Number: 5,576,296
[45] Date of Patent: Nov. 19, 1996

[54] GALANIN ANTAGONIST

[75] Inventors: Tamas Bartfai, Stocksund; Tomas Hökfelt, Djursholm; Ulo Langel, Stockholm; Bo Ahrén; Stefan Lindskog, both of Lund, all of Sweden; Silvana Consolo, Milan, Italy; Tiit Land; Zsuzsanna Wiesenfeld-Hallin, both of Stockholm, Sweden

[73] Assignee: Aktiebolaget Astra, Sodertalje, Sweden

[21] Appl. No.: 468,514

[22] Filed: Jun. 6, 1995

Related U.S. Application Data

[63] Continuation of Ser. No. 146,139, Nov. 12, 1993, abandoned.

[30] Foreign Application Priority Data

May 15, 1991 [SE] Sweden .................................. 9101472

[51] Int. Cl.$^6$ .............................. C07K 5/00; C07K 7/00; C07K 17/00; A61K 38/00
[52] U.S. Cl. .............................. 514/13; 530/326; 530/325
[58] Field of Search .............................. 514/13; 530/326, 530/325

[56] References Cited

PUBLICATIONS

Fisone, et al., *Proc. Natl. Acad. Sci. USA*, vol. 86, pp. 9588–9591 (1989).
Lagny–Pourmir, et al., *Peptides*, vol. 10, pp. 757–761 (1989).
Hermansen, et al, *Acta Endocr. (Copenh)* 121:545–550 (1989).
Dunning, et al., *Diabetes*, vol. 37, pp. 1157–1162 (1988).
Lindskog, et al., *European Journal of Pharmacology*, 210, pp. 183–188 (1992).
Wiesenfeld–Hallin, et al., *Proc. Natl. Acad. Sci. USA*, vol. 89, pp. 3334–3337 (1992).
Bartfai, et al., *Proc. Natl. Acad. Sci. USA*, vol. 88, pp. 10961–10965 (1991).
Cecil Textbok of Medicine, 1992 pp. 2076–2077.

*Primary Examiner*—Toni R. Scheiner
*Assistant Examiner*—Sheela J. Huff
*Attorney, Agent, or Firm*—White & Case

[57] ABSTRACT

A galanin antagonist which is a galanin receptor ligand is described. New peptides, Galanin (1-12)-Pro-Substance P(5-11), Galanin (1-12)-Pro-Bradykinin(2-9), Galanin (1-12)-Pro-Pro-Pro- (Leu$^5$-Enkephalin (5-1), Galanin (1-12)-Pro-Lys(ε-NH-)Pro-(Leu5-Enkephalin (5-1) and functional analogues and functional derivatives thereof are disclosed. The peptides are used in pharmaceutical preparations to treat a disorder in a mammal which depends on the physiological function of galanin at the galanin receptor.

5 Claims, No Drawings

GALANIN ANTAGONIST

This application is a continuation of application Ser. No. 08/146,139, filed Nov. 12, 1993, now abandoned.

The present invention relates to a galanin antagonist which is a galanin receptor ligand. Further, it relates to the peptides Galanin(1-12)-Pro-Substance P(5-11), Galanin (1-12)-Pro-Bradykinin (2-9), Galanin (1-12)-Pro-Pro-Pro-(Leu$^5$-Enkephalin (5-1)), Galanin (1-12)-Pro-Lys (ε—NH—Pro-(Leu$^5$-Enkephalin (5-1)) and functional analogues and functional derivatives thereof which exhibit substantially the same galanin antagonistic effect as said peptides. Use of the galanin antagonist, a pharmaceutical preparation comprising it and a method of treating a disorder in a mammal which depends on the physiological function of galanin at the galanin receptor are also included.

BACKGROUND

Neuro-transmitters and hormones can induce their cellular effects by binding to and activating membrane bound receptors. The neuro-peptide galanin was isolated in 1983 from porcine upper intestine and was found to contain 29 amino acid residues (Tatemoto, K., et al, FEBS Lett., 164 (1983) 124–128). The sequences of galanin from two other mammals, rat and cow, have been described (Vrontakis M. E., et al, J. Biol. Chem. 262(1987) 16755–16758; Kaplan L. M. et al, Proc. Natl. Acad. Sci. U.S.A. 85(1988) 1065–1069 and Rokaeus Å. and Carlquist M., FEBS Lett. 234 (1988) 400–406). A comparison of the peptide sequence of galanin from the mammals rat, porcine and bovine reveals that the N-terminal amino acids 1–15 are identical. Thus, it is most likely that said conserved region will be found in galanin from other mammals, including man.

Galanin has a wide pattern of distribution, often correlating with multiple neuro-formula actions exerted in a variety of different systems.

Hitherto no galanin antagonists, which are galanin receptor ligands, have been reported. A galanin antagonist would be a useful tool in determining the physiological significance of galanin and to develope pharmaceutical preparations for the regulation of the physiological function of galanin at the galanin receptor.

DESCRIPTION OF THE INVENTION

One aspect of the invention is directed to a galanin antagonist which is a galanin receptor ligand. Thus, the antagonistic effect of the galanin antagonist according to the invention is exercised at galanin receptors. In an embodiment of this aspect of the invention the antagonist is selected from the group consisting of the peptides H—Gly—Trp—Thr—Leu—Asn—Ser—Ala—Gly—Tyr—Leu—Leu—Gly—Pro—
—Gln—Gln—Phe—Phe—Gly—Leu—Met—X, (SEQ ID NO:1)

H—Gly—Trp—Thr—Leu—Asn—Ser—Ala—Gly—Tyr—Leu—Leu—Gly—Pro—
—Pro—Pro—Gly—Phe—Ser—Pro—Phe—Arg—X, (SEQ ID NO:2)

H—Gly—Trp—Thr—Leu—Asn—Ser—Ala—Gly—Tyr—Leu—Leu—Gly—Pro—
—Pro—Pro—Leu—Phe—Gly—Gly—Tyr—X, (SEQ ID NO:3)

H—Gly—Trp—Thr—Leu—Asn—Ser—Ala—Gly—Tyr—Leu—Leu—Gly—Pro—
—Lys—X
  |
  Pro—Leu—Phe—Gly—Gly—Tyr—H wherein X represents —NH$_2$ or —OH (amide or free acid), and functional analogues and functional derivatives thereof.

In the specification and claims, it is intended that "functional analogues" of the peptides of the invention i.a. should comprise shorter of longer peptides, with or without substitution of one or several amino acid residues for other amino acid residues, as long as such analogues exhibit substantially the same pharmacological function as the peptides of the invention, i.e. are galanin antagonists at the galanin receptor.

Further, it is intended that "functional derivatives" of the peptides according to the invention comprise any compound which exhibits substantially the same pharmacological function as the peptides of the invention, i.e. is a galanin antagonist at the galanin receptor. Specifically, such a compound could be one which is derived from one of the peptides of the invention, but wherein one or several amino acid residues are substituted for other chemical groups, i.e. organic as well as inorganic molecules or elements resulting in a "peptidomimetic".

It is believed that it is the structural conformation at the galanin receptor of a peptide according to the invention which is responsible for its pharmacological function as a galanin antagonist and for its affinity to the galanin receptor (thus being a galanin receptor ligand).

Thus, it is believed that the functional derivatives and the functional analogues comprised by the invention should have a similar structural conformation at the galanin receptor as the peptides of the invention. The surrounding of the galanin receptor could be mimicked by e.g. blood or physiological saline solution.

Another aspect of the invention is directed to the peptides

H—Gly—Trp—Thr—Leu—Asn—Ser—Ala—Gly—Tyr—Leu—Leu—Gly—Pro—
—Gln—Gln—Phe—Phe—Gly—Leu—Met—X,  (SEQ ID NO:1)

H—Gly—Trp—Thr—Leu—Asn—Ser—Ala—Gly—Tyr—Leu—Leu—Gly—Pro—
—Pro—Pro—Gly—Phe—Ser—Pro—Phe—Arg—X,  (SEQ ID NO:2)

H—Gly—Trp—Thr—Leu—Asn—Ser—Ala—Gly—Tyr—Leu—Leu—Gly—Pro—
—Pro—Pro—Leu—Phe—Gly—Gly—Tyr—X,  (SEQ ID NO:3)

H—Gly—Trp—Thr—Leu—Asn—Ser—Ala—Gly—Tyr—Leu—Leu—Gly—Pro—
—Lys—X
   |
   Pro—Leu—Phe—Gly—Gly—Tyr—H wherein X represents —NH$_2$ or —OH (amide or free acid), and functional analogues and functional derivatives thereof which exhibit substantially the same galanin antagonistic effect as said peptides.

As mentioned above, the peptides may also be named Galanin-(1-12)-Pro-Substance P(5-11), Galanin(1-12)-Pro-Bradykinin(2-9), Galanin(1-12)-Pro-Pro-Pro-(Leu$^5$-Enkephalin(5-1)) and Galanin(1-12-Pro-Lys(ε-NH-)Pro(Leu$^5$-Enkephalin(5-1)), respectively.

In the experimental part of this specification the above listed peptides, in amide form (i.e. X=—NH$^2$), have been named M15, M35, M36, A and M34, A, respectively.

Functional analogs may be peptides such as

H—Gly—Trp—Thr—Leu—Asn—Ser—Ala—Gly—Tyr—Leu—Leu—Gly—Pro—
(D—Arg)—Pro—Lys—Pro—Gln—Gln—(D—Trp)—Phe—(D—Trp)—Leu—Leu—X

H—Gly—Trp—Thr—Leu—Asn—Ser—Ala—Gly—Tyr—Leu—Leu—Gly—Pro—
—Ala—Leu—Ala—Leu—Ala—Leu—Ala—X  (SEQ ID NO:5)

H—Gly—Trp—Thr—Leu—Asn—Ser—Ala—Gly—Tyr—Leu—Leu—Gly—Pro—
—Pro—Pro—Ala—Leu—Ala—Leu—Ala—X  (SEQ ID NO:6)

H—Gly—Trp—Thr—Leu—Asn—Ser—Ala—Gly—Tyr—Leu—Leu—Gly—Pro—
—Pro—Gly—Phe—Ser—Pro—Phe—Arg—X  (SEQ ID NO:7)

H—Gly—Trp—Thr—Leu—Asn—Ser—Ala—Gly—Tyr—Leu—Leu—Gly—Pro—
—Arg—His—Tyr—Ile—Asn—Leu—Ile—Thr—Arg—Gln—Arg—Tyr—X  (SEQ ID NO:8)

H—Gly—Trp—Thr—Leu—Asn—Ser—Ala—Gly—Tyr—Leu—Leu—Gly—Ala—
—Arg—His—Tyr—Ile—Asn—Leu—Ile—Thr—Arg—Gln—Arg—Tyr—X  (SEQ ID NO:9)

H—Gly—Trp—Thr—Leu—Asn—Ser—Ala—Gly—Tyr—Leu—Leu—Gly—Pro—
—Pro—Pro—Tyr—Gly—Gly—Phe—Leu—X  (SEQ ID NO:10)

H—Gly—Trp—Thr—Leu—Asn—Ser—Ala—Gly—Tyr—Leu—Leu—Gly—Pro—
—Pro—Pro—Leu—Phe—Gly—Gly—Tyr—X  (SEQ ID NO:3)

wherein X represents —NH2 or —OH (amide or free acid).

A further aspect of the invention is directed to the use of a galanin antagonist which is a galanin receptor ligand for the preparation of a pharmaceutical preparation. It can be mentioned that the above listed peptides are soluble in water, which facilitates the preparation of a pharmaceutical preparation for injection.

Yet another aspect of the invention is directed to a galanin antagonist which is a galanin receptor ligand for use in a pharmaceutical preparation.

Yet a further aspect of the invention is directed to a pharmaceutical preparation comprising a galanin antagonist which is a galanin receptor ligand as an active ingredient, together with pharmaceutically acceptable additive(s). Depending on the specific type of pharmaceutical preparation to be prepared, such additive(s) should be chosen to make up the desired preparation. Suitable additive(s) for the specific type of preparation to be prepared, such as solutions for injection, tablets or plasters, can be found in the U.S. Pharmacopoeia.

Thus the present invention also provides compositions containing an effective amount of compounds of the present invention, including the nontoxic addition salts, amides and esters thereof, which may, alone, serve to provide the above-recited therapeutic benefits. Such compositions can also be provided together with physiologically tolerable liquid, gel or solid diluents, adjuvants and excipients.

These compounds and compositions can be administered to mammals for veterinary use, such as with domestic animals, and clinical use in humans in a manner similar to other therapeutic agents. In general, the dosage required for therapeutic efficacy will range from about 0.01 to 1000 mcg/kg, more usually 0.1 to 1000 mcg/kg of the host body weight. Alternatively, dosages within these ranges can be administered by constant infusion over an extended period of time until the desired therapeutic benefits have been obtained.

Typically, such compositions are prepared as injectables, either as liquid solutions or suspensions; solid forms suitable for solution in, or suspension in, liquid prior to injection may also be prepared. The preparation may also be emulsified or incorporated in drug delivery systems like liposomes or microspheres. The active ingredient is often mixed with diluents or excipients which are physiologically tolerable and compatible with the active ingredient. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH-buffering agents, and the like.

The compositions are conventionally administered parenterally, by injection, for example, either subcutaneously, intramuscularly, intraperitoneally or intravenously.

Additional formulations which are suitable for other modes of administration include suppositories, vagitories, intranasal aerosols, buccal formulations like adhesive tablets, gels or patches and in some cases, oral formulations. For suppositories and vagitories, traditional binders and excipients may include, for example, polyalkylene glycols or triglycerides; such suppositories may be formed from mixtures containing the active ingredient in the range of 0.5% to 10% preferably 1%–2%. Oral formulations include such normally employed excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained-release formulations, or powders, and contain 10%–95% of active ingredient, preferably 25%–70%.

The peptide compounds may be formulated into the compositions as neutral or salt forms. Pharmaceutically acceptable nontoxic salts include the acid addition salts (formed with the free amino groups) and which are formed with inorganic acids such as, for example, hydrochloric or phosphoric acids, or organic acids such as acetic, oxalic, tartaric, mandelic, and the like. Salts formed with the free carboxyl groups may be derived from inorganic bases such as, for example, sodium, potassium, ammonium, calcium, or ferric hydroxides, and such organic bases as ispropylamine, trimethylamine, 2-ethylamino ethanol, histidine, procaine, and the like.

Still another aspect of the invention is directed to a method of treating a disorder in a mammal which depends on the physiological function of galanin at the galanin receptor, which comprises administering to said mammal a pharmacologically effective amount of a galanin antagonist which is a galanin receptor ligand. Since the physiological function of galanin at the galanin receptor is specific for each individual, the pharmacologically effective amount of a galanin antagonist which is to be administered to treat a disorder in a mammal has to be decided by a physician or veterinary on an individual bases.

Galanin antagonists would be useful in the regulation of at least the following:

insulin release, growth hormone release, acetylcholine release, dopamine release, Substance P release, Somatostatin release, Noradrenaline release.

At present, the presumed fields of medical indication are endochrinology, food intake, neurology and psychiatry: senile dementia of Alzheimer's type, schizophrenia, analgesia, intestinal diseases.

Preparation of a Galanin Antagonist According to the Invention

Conventional methods of preparing peptides can be used to prepare the galanin antagonists of the invention, suitably modified if the antagonist is a peptidomimetic. In addition to liquid phase synthesis, conventional procedures for synthesizing the novel compounds of the present invention include any solid phase peptide synthesis method. In such a method the synthesis of the novel compounds can be carried out by sequentially incorporating the desired amino acid residues one at a time into the growing peptide chain according to the general principles of solid phase methods.

Abbreviations used in the following:
NMP=N-Methylpyrrolidone
HOBt=N-hydroxybenzotriazole
MBHA=p-Methylbenzhydrylamine
PAM=p-Acetoxymethyl
Boc=tert-Butyloxycarbonyl
DMSO=Dimethylsulfoxide
DIEA=diisopropylethylamine
Tos=tosyl
OcHex=cyclohexyl ester
4—MeBzl=4-methylbenzyl
OBzl=bensyl ester
Bom=t-Benzyloxymethyl
Clz=2-Chlorobenzyloxycarbonyl
Bzl=O-benzyl
For=formyl
Brz=2-bromobenzyloxycarbonyl
TFA=trifluoroacetic acid
DMS=dimethyl sulfid
DCM=dichloromethan
DMF=N,N-dimethylformamide The peptides "M15", "M35" and "M36,A" of this invention were assembled in a step-wise manner on a solid support using an Applied Biosystems Model 431A Peptide Synthesizer using the standard NMP/HOBt Solvent-Activation strategy on a 0.1 mmole scale (small scale).

The peptide "M34,A" was synthesized in the same manner, except for the protective group which was ε-Fmoc and Boc for Lys. Accordingly one part of the peptide was synthesized using Boc-chemistry, and the other part was synthesized using Fmoc chemistry.

The functional derivatives of the invention were prepared in analogous manner.

tert-Boc-amino acids were coupled to tert-Boc-amino acid-PAM (Nova Chemical Company Ltd., UK) resin for fee acid (X=—OH) or MBHA(Bachem Feinchemikalien AG, Switzerland) resin for amide (X=—NH$_2$) as hydroxybenzotriazole(HOBt) esters.

As individual cycle for each amino acid included deprotection of the tert-Boc-group with 50% trifluoroacetic acid in CH$_2$Cl$_2$(DCM) for 19 min, and acylation with 10-fold excess (compared to the amount of amino groups on a resin) of the protected amino acids in a mixture of 15% DMSO in N-methyl pyrrolidone (NMP) for 35 min. Between each operation several extensive washings were performed with CH$_2$Cl$_2$, DIEA and NMP. After each coupling acetylation (capping) was carried out using 10% acetic anhydride and 5% DIEA in NMP for 5 min.

With the excention of Boc-Lys(Fmoc) in the case of the peptide 34,A, all amino acids used were tert-Boc-protected at the N-terminal (obtained from Nova Chemical Company Ltd., UK), and their reactive side chains were protected with Tos in Arg, OcHex in Asp, 4-MeBzl in Cys, OBzl in Glu, Bom in His, ClZ in Lys, Bzl in Ser and Thr, For in Trp, and Brz in Tyr.

All the solvents and other reagents for automatic peptide synthesis were from Applied Biosystems.

The reagents used in deprotection and cleavage steps were of analytical grade and used without further purification:

1,2-ethanediitol, acetic anhydride, trifluoromethyl sulfonic acid (TFMSA), dimethyl sulfide (DMS) and p-cresol from Fluka, diethyl ether and acetonitrile from Merck and HF from AGA Gas.

The fully assembled peptide-resins were dried under high vacuum overnight. Deprotection from formyl-group on Trp and benzyl-groups was performed using "low TFMSA" method. For that 100 mg of peptide-resin was treated with 2 ml of the mixture of TFMSA(10%), TFA(50%), DMS(30%), p-cresol(8%) and dimercaptoethan(2%) for 2 h at 0° C. while shaking, the procedure was followed by washing with EtOH, DCM, DMF, DIEA/DCM, DMF and DCM.

After drying under vacuum the peptide was cleaved from resin and deprotected by mixing of 10 ml liquid HF (containing 20% of 1:1 mixture of p-cresol and p-thiocresol) with 1 g of peptide-resin at 0° C. for 60 min. The resin was washed 2 times with 10 ml of $Et_2O$, peptide extracted with 20% acetonitrile/water and filtered. Lyophilization of the aqueous filtrate yielded the crude peptide.

Preparative purifications were carried out on the crude product by HPLC on reversed phase C18 column. 10 mg of crude peptide was dissolved in 1 ml of 20% acetonitrile/water and eluted with a gradient (45 min) of 20–60% mixture of 0.1% TFA/acetonitrile in 0.1 & TFA/water at a flow rate of 2.0 ml/min. The fractions were collected according to the absorption detected at 238 nm.

Purity of the individual peptides was checked by analytical HPLC and determined to be 99%. Molecular weights of the peptides were determined using Plasma Desorption Mass Spectrometer (PDMS) Model Bioion 20, Applied Biosystems, the calculated molecular weight values were obtained in each case for the purified peptide.

TABLE

Purity of the individual peptides was checked by analytical HPLC and determined to be 99 %. Molecular weights of the peptides were determined using Plasma Desorption Mass Spectrometer (PDMS) Model Bioion 20, Applied Biosystems, the expected values were obtained in each case.

Galanin(1–12)-Pro-SP(5–11) amide (M15) (SEQ ID NO:1): (MW = 2199) $IC_{50}$ = 0.1 nM

```
1                                                                              20
Gly—Trp—Thr—Leu—Asn—Ser—Ala—Gly—Tyr—Leu—Leu—Gly—Pro—Gln—Gln—Phe—Phe—Gly—Leu—Met amide
1           5                   10    12         5       7               11
```

Galanin(1–12)-Pro-Spantide amide (C 7): (MW = 2827) $IC_{50}$ = 0.2 nM

```
1                                                    13
Gly—Trp—Thr—Leu—Asn—Ser—Ala—Gly—Tyr—Leu—Leu—Gly—Pro—(D—Arg)—Pro—Lys—Pro—Gln—Gln—(D—Trp)—
    22   23  24                                                     spantide
Phe—(D—Trp)—Leu—LeuNH2
```

Galanin(1–12)-Pro—Pro—Pro-SP(5–11) amide (M37) (SEQ ID NO:11): (MW = 2392) $IC_{50}$ = 40 nM

```
1           5                       12                                          22
Gly—Trp—Thr—Leu—Asn—Ser—Ala—Gly—Tyr—Leu—Leu—Gly—Pro—Pro—Pro—Gln—Gln—Phe—Phe—Gly—Leu—Met amide
                                             5                               11
```

Galanin(1–13)-Ala—Leu—Ala—Leu—Ala—Leu—Ala amide (M 38) (SEQ ID NO:5): (MW = 1970) $IC_{50}$ = 0.2 nM

```
1           5                           13                      20
Gly—Trp—Thr—Leu—Asn—Ser—Ala—Gly—Tyr—Leu—Leu—Gly—Pro—Ala—Leu—Ala—Leu—Ala—Leu—Ala amide
```

Galanin(1–12)- -Pro—Pro—Pro—Ala—Leu—Ala—Leu—Ala amide (M 40) (SEQ ID NO:6): (MW = 1980) $IC_{50}$ = 13 nM

```
1           5                           13                      20
Gly—Trp—Thr—Leu—Asn—Ser—Ala—Gly—Tyr—Leu—Leu—Gly—Pro—Pro—Pro—Ala—Leu—Ala—Leu—Alaamide
```

Galanin(1–13)-Bradykinin(3–9) amide (M20) (SEQ ID NO:7): (MW = 2135) $IC_{50}$ = 1 nM

```
1                                       13                      20
Gly—Trp—Thr—Leu—Asn—Ser—Ala—Gly—Tyr—Leu—Leu—Gly—Pro—Pro—Gly—Phe—Ser—Pro—Phe—Arg amide
                                                     3                       9
```

Galanin(1–13)-Bradykinin(2–9) amide (M 35) (SEQ ID NO:2): (MW = 2232) $IC_{50}$ = 0.2 nM

```
1                                       13                          21
Gly—Trp—Thr—Leu—Asn—Ser—Ala—Gly—Tyr—Leu—Leu—Gly—Pro—Pro—Pro—Gly—Phe—Ser—Pro—Phe—Arg amide
                                                     2                           9
```

Galanin(1–13)-NPY(25–36) amide (M 32) (SEQ ID NO:8): (MW = 2961) $IC_{50}$ = 0.05 nM

```
1                                       13                                          25
Gly—Trp—Thr—Leu—Asn—Ser—Ala—Gly—Tyr—Leu—Leu—Gly—Pro—Arg—His—Tyr—Ile—Asn—Leu—Ile—Thr—Arg—Gln—Arg—Tyr
                                                                                                amide
                                                     25                                         36
```

Galanin(1–12)-Ala-NPY(25–36) amide (M 88) (SEQ ID NO:9): (MW = 2935) $IC_{50}$ = 1 nM

```
1                                       13                                          25
Gly—Trp—Thr—Leu—Asn—Ser—Ala—Gly—Tyr—Leu—Leu—Gly—Ala—Arg—His—Tyr—Ile—Asn—Leu—Ile—Thr—Arg—Gln—Arg—Tyr
                                                                                                amide
                                                     25                                         36
```

TABLE-continued

Purity of the individual peptides was checked by analytical HPLC and determined to be 99 %. Molecular weights of the peptides were determined using Plasma Desorption Mass Spectrometer (PDMS) Model Bioion 20, Applied Biosystems, the expected values were obtained in each case.

Galanin(1–12)-Pro—Pro—Pro-Leuenkephalin(1–5) amide (M 36) (SEQ ID NO:10): (MW = 2078) $IC_{50}$ = 40 nM

```
1                                             12                                          20
Gly—Trp—Thr—Leu—Asn—Ser—Ala—Gly—Tyr—Leu—Leu—Gly—Pro—Pro—Pro—Tyr—Gly—Gly—Phe—Leu amide
                                              1                           5
```

Galanin(1–12)-Pro—Pro—Pro-Leuenkephalin(5–1) amide (M36,A) (SEQ ID NO:3): (MW = 2078) $IC_{50}$ = 20 nM

```
1                                             12                                          20
Gly—Trp—Thr—Leu—Asn—Ser—Ala—Gly—Tyr—Leu—Leu—Gly—Pro—Pro—Pro—Leu—Phe—Gly—Gly—Tyr amide
                                              5                           1
```

Galanin(1–13)-Lys amide (Pro-Leuenkephalin(5–1)) (M34,A) (MW = 2223) $IC_{50}$ = 10 nM

```
1                                          13  14
Gly—Trp—Thr—Leu—Asn—Ser—Ala—Gly—Tyr—Leu—Leu—Gly—Pro—Lys amide
N-teminus                                      |
                                               Pro—Leu—Phe—Gly—Gly—Tyr
                                               5                    1
```

$IC_{50}$ has been determined in displacement experiments in rat hypothalamus

PHARMACOLOGICAL EXPERIMENTS

1) Galanin inhibits glucose-induced insulin release, measured according to Ahrén, B., et al (Biochemical and Biophysical Research Communications, Vol. 140. No. 3, 1986, 1059–1063). By using the same procedure as the cited Ahrén B., et al, a peptide according to the invention, M15, is now shown to block the galanin-inhibited insulin release in equimolar concentration.

Animals and Preparation of Cells

Adult obese hyperglycemic mice (ob/ob) of both sexes were taken from a local non-inbred colony and starved overnight. The animals were killed by decapitation and the islets were isolated by collagenase isolation technique. A cell suspension was prepared essentially as described by Lehrnmark, Å., in Diabetologia 10, 1974, 431–438. Briefly, the islets were dissociated into single cells and small clusters by shaking in a $Ca^{2+}$-$Mg^{2+}$-deficient medium supplemented with EGTA (Ethylene glycol-bis(beta-aminoethyl ether)N, N,N',N',-tetra-acetic acid, SIGMA). Thereafter, the cells were incubated at 37° C., pH 7.4, overnight in 12 ml RPMI 1640 medium (Tissue culture medium from SIGMA, which contains L-glutamine and does not contain sodium bicarbonate) supplemented with 10% NU-serum TM (Collaborative Research Inc., Lexington, Mass., U.S.A.), 100 IU/ml penicillin, 60 µg/ml gentamycin and 100 µg/ml streptomycin. To avoid attachment of the cells to the culture flasks during incubation, the suspension was shaken gently.

Media

The basal medium used was a HEPES buffer (N-[2Hydroxyethyl]-piperazine-N'-[2-ethanesulfonic acid], SIGMA), pH 7.4, physiologically balanced in cations with $Cl^-$ as the sole anion. In all cases the basal medium was supplemented with 1 mg/ml albumin.

Measurements of Insulin Release

The kinetics of insulin release were studied by perfusing pancreatic beta-cells (approx. $1\times10^6$) with 20 mM or 5 mM glucose mixed with Bio-Gel P-4 polyacrylamide beads (200–400 mesh, Bio-Rad Lab., Richmond, Calif., U.S.A.) in a 0.5 ml column. The flow rate was 0.5 ml/min and 1–3 min fractions were collected and analyzed for insulin radioimmunologically, using crystalline rat insulin as a reference.

Results

After 60 min incubation in the presence of glucose (8.3 mM), galanin ($10^{-7}$M) completely abolished insulin release from 34±2 µU/ml to 3±1 µU/ml (P <0.001; N=32). The peptide of the invention, M 15, alone ($10^{-6}$M–$10^{-9}$M) dose-dependently counteracted the galanin-induced inhibition of insulin release.

Insulin release in the presence of glucose, galanin and M15 at $10^{-6}$M, $10^{-7}$ or $10^{-8}$ was 28±2 µU/ml (N=16), 17±4 µU/ml (N=16), and 10±3 µU/ml (N=16), respectively. M15 at $10^{-9}$M was without effect.

As a result of the above experiments it can be concluded that the peptide of the invention, M15, counteracts the galanin-induced inhibition of insulin release in islets.

2) Galanin inhibits acetylcholine release, measured according to Fisone G., et al (Proc. Natl. Acad. Sci. vol 84, 1987, 7339–7343). By using substantially the same procedure as the cited Fisone G., et al, a peptide according to the invention, M15, is now shown to counteract the inhibitory effects of galanin on the scopolamine-induced release of acetylcholine in vivo.

Microdialysis Experiments

Surgery and basic methodology. Experiments were carried out with female CD-COBS (Charles River, Como, Italy) rats, weighing 200–260 g. Animals were anesthetized with equitensin (1% pentobarbital, 4% chloral hydrate). Guide cannula was implanted stereotoxically into the ventral hippocampus according to the following coordinates from the atlas of Paxinos and Watson (Paxinos G. and Watson C. (1986) The Rat Brain in Stereotoxic Coordinates, 2nd edn. Academic Press, Sydney.): 5 mm posterior to the bregma, 4.0 mm lateral to the midline, and 6.8 mm below the surface of the dura mater. A styler was then inserted to keep the guide cannula patent until the next day. At the time the styler was removed and replaced with a microdialysis probe (CMA 10, Carnegie Medicine AB, Stockholm, Sweden) containing a membrane having an exposed area of 3×0.5 mm. The microdialysis probe extended 3 mm beyond the end of the guide cannula; it was perfused at a constant rate of 2 μl (min with Ringer's solution (NaCl, 147 mM; $CaCl_2$, 2.2 mM and KCl, 4.0 mM), containing 10 μM physostigmine sulfate and adjusted to pH 7.0 with NaOH. The initial 40 min perfusate was discarded. Thereafter, perfusates were collected every 20 min during a total perfusion period of 260 min. At the end of the collection period, the samples were immediately frozen on solid $CO_2$ and lyophilized. Acetylcholine (Ach) content was quantified by a specific radioenzymatic method described in detail by Consolo S., et al. (J. Neurochem. 48, (1987), 1459–1465.) and Wu C. F., et al (Neurobiol. Aging 9, (1988), 357–361.) and involving (a) the conversion of choline to phosphorylcholine in the presence of choline phosphokinase and ATP, (b) the enzymatic hydrolysis of acetylcholine to choline and acetic acid, (c) the reacetylation of the resulting choline to $[^3H]$acetylcholine with the addition of $[^3H]$acetylcoenzyme-A, 99.9 GBq/mmol, and acetylcoenzyme A:ChAT, and (d) the separation and scintillation counting of the resulting $[^3H]$acetylcholine by extraction into tetraphenylboron-containing ketone phase by liquid—liquid ion exchange chromatography. Phosphorylation, hydrolysis and acetylation reactions were validated routinely.

The concentration of acetylcholine in each sample was calculated by linear regression based on the radioactivity of the standards (linear from 10 fmol-25 pmol acetylcholine) with the slope equal to 7800 net dpm/pmol. The coefficient of variation of the replicate perfusate samples or acetylcholine standards was approximately 3%.

In vitro recovery of acetylcholine through three dialysis tubings was determined as previously described (Wu et al., ibid). The average recovery was 17.6±0.5%.

At the termination of the release experiments, the placements of the dialysis probes were verified histologically by use of staining for Nissl substance.

Effect of galanin and M 15 on the scopolamine-induced release of ACh, measured "in vivo" from the rat ventral hippocampus

| | |
|---|---|
| Saline | 2.0 pmoles |
| Scopolamine | 13.1 pmoles |
| Scopolamine + Galanin | 6.9 pmoles |
| Scopolamine + M15 | 9.4 pmoles |

Galanin (1.56 nmoles) and M15 (3.12 nmoles) were injected i.c.v. 2 min before scopolamine (0.3 mg/kg, s.c.). ACh release was measured in the perfusate collected during the following 80 min, in four 20 min-fractions. The values are expressed as pmoles of ACh measured during the 20 min fraction corresponding to the peak of the scopolamine-effect and corresponding to the second 20 min-fraction. The data are the means of experiments carried out in two rats (n=2).

As a result of the above experiments it can be concluded that the peptide of the invention, M15, counteracts the galanin-induced inhibition of scopolamine-induced release of acetylcholine in hippocampus.

3) Effects of intrathecal galanin and C-fiber stimulation on the flexor reflex has been described by Wiesenfeld-Hallin Z., et al (Brain Res. 486 (1989)205–213). By using substantially the same procedure as the cited reference, a peptide according to the invention, M15, is shown to have an antagonistic effect on intrathecal galanin-induced facilitation of the flexor reflex. An other peptide of the invention, M35, has given similar results in preliminary experiments.

Electrophysiological Study

In acute experiments, the magnitude of the polysynaptic hamstring flexor reflex in response to activation of high threshold afferents was examined in decerebrated, spinalized, unanaesthetized rats by recording the electromyogram (EMG) from the posterior biceps femoris/semitendinosus muscles. The animals were briefly anaesthetized with Brietal®, and a tracheal cannula was inserted. The rats were mounted in a stereotaxic frame, decerebrated by aspiration of the forebrain and midbrain and then ventilated. The spinal cord was exposed by laminectomy at thoracic level and sectioned at $Th_{8-9}$. An i.t. catheter (PE 10) was implanted caudally to the transection with its tip on the left side of the lumbar spinal cord ($L_{4-5}$). The flexor reflex was elicited by test stimuli to the sural nerve or its innervation area with single electric shocks (0.5 ms, 10 mA) of sufficient strength to activate C-fibres (Wall and Woolf, 1984). In some experiments a CS (conditioning stimulus) (1 Hz, 20 s) of the same strength as the test stimuli was administered to the sural nerve.

The flexor reflex was recorded as EMG activity via stainless steel needle electrodes inserted in the ipsilateral hamstring muscles. The number of action potentials elicited during the reflex was integrated over 2 s. The integrated reflex was recorded on a Gould chart recorder (Model 2400 S). During the experiments the heart rate and rectal temperature of the rat were monitored and maintained within normal limits. The proper location of the i.t. catheter was confirmed after each experiment by laminectomy.

Galanin (Bachem, Bubendorff, Switzerland) and Somatostatin (Ferring, Malmö, Sweden) were dissolved in 0.9% saline. All peptides were injected i.t. in a volume of 10 μl followed by 10 μl saline to flush the catheter.

Data Collection

A stable baseline reflex magnitude was established for at least 20 min before each i.t. injection or nerve CS. The effect of i.t. peptides or the nerve CS on the flexor reflex was expressed as percent change in reflex magnitude compared to baseline which was defined as 100%. To test the interaction of galanin with other peptides or the sural CS, it was administered 15 min prior to the injection of the other peptides when the facilitatory effect of galanin had subsided or simultaneously with the sural CS.

The antagonistic effect of intrathecal (i.t.) M-15 on the i.t. galanin-induced facilitation of the flexor reflex was measured. The peak facilitatory effect of 30 pmol galanin was 167.0±42.8% over baseline reflex magnitude. The antagonism of M-15, injected 5–10 min after galanin was calculated as the percentage reduction of the peak facilitatory effect of galanin. Data is expressed as meant S.E.M.

| Dose of M-15 | n | % antagonism |
|---|---|---|
| 30 pmol | 4 | 35.8 ± 20.7 |
| 300 pmol | 4 | 79.3 ± 8.4 |
| 3 nmol | 3 | 93.0 ± 3.4 |

The experiments were repeated using the peptide of the invention, M35, and similar results were achieved.

As a result of the above experiments it can be concluded that peptides of the invention counteract the intrathecal galanininduced facilitation of the flexor reflex in a dose-dependent manner.

4) Ligand binding studies were conducted. Displacement of $^{125}$I-galanin by galanin, galanin fragment (1-13), Substance P fragment (4-11), galanin fragment (1-13) + Substance P fragment (4-11) in equimolar concentrations and the peptides of the invention M15, M35 and M34, A was studied. The peptides of the invention proved to bind specifically to the galanin receptor.

Preparation of $^{125}$I-monoiodo-Tyr$^{26}$-Porcine Galanin

Synthetic porcine galanin(1-29) was iodinated by chloramine-T-method to yield $^{125}$I-monoiodo-Tyr$^{26}$-porcine galanin (specific activity 1800–2000 Ci/mmol), (as described by Land T., et al in: Methods in Neurosciences, Ed. M. Conn, 5, 1991, 225–234), and employed in ligand binding studies carried out at equilibrium.

Preparation of Membrane Fraction of Rin m 5F Cells

The establishment and cell culture of Rin m 5F (a rat pancreatic β-tumor cell-line) cells have been described earlier (Gazdav A. F., et. al. Proc. Natl. Acad. Sci. USA, 77 (1980) 3519–3523). Briefly, the cells were grown in RPMI-1640 (Gibco) medium containing 10% (v/v) fetal calf serum, 2.06 mM L-gluthamine, 100 IU/ml penicillin and 100 μg/ml streptomycin in 10% $CO_2$-90% air 37° C. They were passaged every 5 days. The cells were detached from the surface of the bottles using 0.25% trypsin containing 1 mM EDTA and centrifuged at 2000 × g for 5 min at 4° C. The pellet was exposed for 15 min to hypoosmotic 5 mM HEPES buffer (pH 7.4). The suspension was centrifuged at 20000 × g for 15 min, the resulting pellet was resuspended in bacitracin-containing (1 mg/mg) 5 mM HEPES-buffered Krebs-Ringer solution (137 mM NaCl, 2.68 nM KCl, 1.8 mM $CaCl_2$, 1 g/l glucose), pH 7.4, and used immediately in equilibrium binding experiments.

Displacement of $^{125}$I-galanin by Galanin and Galanin Receptor Ligands

Displacement experiments were carried out in a final volume of 400 μl of bacitracin-containing (1 mg/ml) HEPES-buffered (5 mM) Krebs-Ringer solution, 0.05% (w/v) of BSA (pH 7.4) in the presence of 0.1–0.2 nM $^{125}$I-galanin, the membrane preparation and the increasing concentrations ($10^{-12}$–$10^{-6}$M) of unlabeled porcine galanin or of other galanin receptor ligands. Samples were incubated for 30 min at 37° C. Incubation was terminated by the addition of 10 ml of ice-cold HEPES-buffered Krebs-Ringer solution, followed by rapid filtration over Whatman GF/C filters, precoated for 5–6 hours in 0.3% (v/v) of polyethyleneimine solution. Filters were washed with 10 ml of assay solution. Radioactivity retained on the filters was determined in a Packard gamma counter. Specific binding was defined as that displaceable by 1 μM galanin (or appropriate concentration of a displacer).

The $IC_{50}$ values of the displacing ligands were calculated from the computer-generated $IC_{50}$ values as described by Land, T., et. al. (ibid).

Fitting of the experimental data was carried out on a Macintosh SE by means of a nonlinear least squares method using the Macintosh program "KaleidGraph".

| Displacement of $^{125}$I-galanin from membranes of Rin m 5F by galanin receptor ligands | |
|---|---|
|  | $IC_{50}$ |
| Galanin (1–29) | 1 nM |
| M15 | 0.1 nM |
| Galanin fragment (1–13) | 100 nM |
| Substance P fragment (4–11) | no displacement > 10 μm |
| Galanin fragment (1–13) + Substance P fragment (4–11) in equimolar concentrations | 100 nM |
| M35 | 0.1 nM |
| M34,A | 10 nM |

As is evident from the above experiments, the peptides of the invention are galanin receptor ligands.

The pharmacological experiments 1), 2) and 3) thus show that the peptides of the invention are galanin antagonists, and the experiment 4) shows that they are galanin receptor ligands. Thus, the galanin antagonists of the invention are galanin receptor ligands, unlike other compounds which earlier have been shown to antagonize a specific effect of galanin in a specific tissue by virtue of interaction with a reaction step beyond the galanin receptor—which was involved in the biological action of galanin in that given cell type. Such antagonism is not specific for galanin action, and is not exerted at galanin receptor. Neither it is applicable to several tissues where galanin acts, whereas the antagonists according to the present invention are bona fide antagonists in the pharmacological meaning and exert their action at the receptor site on the outside of the cell by competing with the endogenous ligand.

Preparation of Membranes from Rat Hypothalamus

Adult male rats (Sprague-Dawley, 180–200 g) were decapitated, the hypothalami quickly dissected and homogenized (10% mass/vol.) in 0.05M TRIS-Cl buffer, pH 7.4. The homogenate was diluted tenfold and centrifuged at 1000 × g for 10 min. The supernatant was centrifuged at 10,000 × g for 45 min and the pellet resuspended in 5 mM Hepes buffered Krebs-Ringer solution (137 mM NaCl, 2.68 mM KCl, 1.8 mM CaCl2 1 g/l glucose), pH 7.4 to yield a final protein concentration of 1.0–1.5 mg/ml.

Ligand Binding Studies in Rat Hypothalamus

Displacement experiments were carried out in a final volume of 400 μl of Hepes-buffered (5 mM) Krebs-Ringer solution, 0.05% (w/v) of BSA (pH 7.4) supplemented with bacitracin (1 mg/ml) in the presence of 0.1–0.2 nM 1251-galanin, the membrane preparation from rat hypothalami and increasing concentrations (10–12, 10–6M) of unlabeled galanin or of other galanin recepto-ligands. Samples were incubated for 30 min at 37° C. Incubation was terminated by the addition of 10 ml of ice-cold Hepes-buffered Krebs-Ringer solution, followed by rapid filtration over Whatman GF/C filters, precoated for 5–6 hours in 0.3% (v/v) of polyethylencimine solution. The filters were washed with 10 ml of assay solution. Radioactivity retained on the filters was determined in a Packard gamma counter. Specific binding was defined as that displaceable by 1 μM galanin. Rat and porcine galanin resulted in indistriguishable displacement curves with the membranes from rat hypothalami.

The 1C50 values of the displacing ligands were calculated by fitting of the experimental data on a Macintosh SE by means of a nonlinear least squares method using the program "KaleidaGraph".

---

We claim:

1. A galanin antagonist which is a galanin receptor ligand, wherein said antagonist is selected from the group consisting of the peptides H—Gly—Trp—Thr—Leu—Asn—Ser—Ala—Gly—Tyr—Leu—Leu—Gly—Pro—Gln—Gln—Phe—Phe—Gly—Leu—Met—X  (SEQ ID NO: 1), H—Gly—Trp—Thr—Leu—Asn—Ser—Ala—Gly—Tyr—Leu—Leu—Gly—Pro—Pro—Pro—Gly—Phe—Ser—Pro—Phe—Arg—X  (SEQ ID NO: 2), H—Gly—Trp—Thr—Leu—Asn—Ser—Ala—Gly—Tyr—Leu—Leu—Gly—Pro—Pro—Pro—Leu—Phe—Gly—Gly—Tyr—X  (SEQ ID NO: 3), and H—Gly—Trp—Thr—Leu—Asn—Ser—Ala—Gly—Tyr—Leu—Leu—Gly—Pro—Lys—X
                                                    |
                                                    Pro—Leu—Phe—Gly—Gly—Tyr—H wherein X represents —NH$_2$ or —OH (amide or free acid), and functional analogues and functional derivatives thereof which exhibit the same galanin antagonistic effect as said peptides.

2. A galanin antagonist according to claim 1 which is selected from the group consisting of the peptides H—Gly—Trp—Thr—Leu—Asn—Ser—Ala—Gly—Tyr—Leu—Leu—Gly—Pro—(D—Arg)—Pro—Lys—Pro—Gln—Gln—(D—Trp)—Phe—(D—Trp)—Leu—Leu—X, H—Gly—Trp—Thr—Leu—Asn—Ser—Ala—Gly—Tyr—Leu—Leu—Gly—Pro—Pro—Pro—Gln—Gln—Phe—Phe—Gly—Leu—Met—X  (SEQ ID NO: 11), H—Gly—Trp—Thr—Leu—Asn—Ser—Ala—Gly—Tyr—Leu—Leu—Gly—Pro—Ala—Leu—Ala—Leu—Ala—Leu—Ala—X  (SEQ ID NO: 5), H—Gly—Trp—Thr—Leu—Asn—Ser—Ala—Gly—Tyr—Leu—Leu—Gly—Pro—Pro—Pro—Ala—Leu—Ala—Leu—Ala—X  (SEQ ID NO: 6), H—Gly—Trp—Thr—Leu—Asn—Ser—Ala—Gly—Tyr—Leu—Leu—Gly—Pro—Pro—

-continued

Gly—Phe—Ser—Pro—Phe—Arg—X   (SEQ ID NO: 7),

H—Gly—Trp—Thr—Leu—Asn—Ser—Ala—Gly—Tyr—Leu—Leu—Gly—Pro—Arg—His—Tyr—Ile—Asn—Leu—Ile—Thr—Arg—Gln—Arg—Tyr—X   (SEQ ID NO: 8),

H—Gly—Trp—Thr—Leu—Asn—Ser—Ala—Gly—Tyr—Leu—Leu—Gly—Ala—Arg—His—Tyr—Ile—Asn—Leu—Ile—Thr—Arg—Gln—Arg—Tyr—X   (SEQ ID NO: 9), and H—Gly—Trp—Thr—Leu—Asn—Ser—Ala—Gly—Tyr—Leu—Leu—Gly—Pro—Pro—Pro—Tyr—Gly—Gly—Phe—Leu—X   (SEQ ID NO: 10)

wherein X represents —$NH_2$ or —OH (amide or free acid).

3. A galanin antagonist according to claim 1 which is selected from the group consisting of the peptides H—Gly—Trp—Thr—Leu—Asn—Ser—Ala—Gly—Tyr—Leu—Leu—Gly—Pro—Gln—Gln—Phe—Phe—Gly—Leu—Met—$NH_2$   (SEQ ID NO: 1), H—Gly—Trp—Thr—Leu—Asn—Ser—Ala—Gly—Tyr—Leu—Leu—Gly—Pro—Pro—Pro—Gly—Phe—Ser—Pro—Phe—Arg—$NH_2$   (SEQ ID NO: 2), H—Gly—Trp—Thr—Leu—Asn—Ser—Ala—Gly—Tyr—Leu—Leu—Gly—Pro—Pro—Pro—Leu—Phe—Gly—Gly—Tyr—$NH_2$   (SEQ ID NO: 3), H—Gly—Trp—Thr—Leu—Asn—Ser—Ala—Gly—Tyr—Leu—Leu—Gly—Pro—Lys—$NH_2$
                               |
           Pro—Leu—Phe—Gly—Gly—Tyr—H, H—Gly—Trp—Thr—Leu—Asn—Ser—Ala—Gly—Tyr—Leu—Leu—Gly—Pro—(D—Arg)—Pro—Lys—Pro—Gln—Gln—(D—Trp)—Phe—(D—Trp)—Leu—Leu—$NH_2$, H—Gly—Trp—Thr—Leu—Asn—Ser—Ala—Gly—Tyr—Leu—Leu—Gly—Pro—Pro—Pro—Gln—Gln—Phe—Phe—Gly—Leu—Met—$NH_2$   (SEQ ID NO: 11), H—Gly—Trp—Thr—Leu—Asn—Ser—Ala—Gly—Tyr—Leu—Leu—Gly—Pro—Ala—Leu—Ala—Leu—Ala—Leu—Ala—$NH_2$   (SEQ ID NO: 5), H—Gly—Trp—Thr—Leu—Asn—Ser—Ala—Gly—Tyr—Leu—Leu—Gly—Pro—Pro—Pro—Ala—Leu—Ala—Leu—Ala—$NH_2$   (SEQ ID NO: 6), H—Gly—Trp—Thr—Leu—Asn—Ser—Ala—Gly—Tyr—Leu—Leu—Gly—Pro—Pro—Gly—Phe—Ser—Pro—Phe—Arg—$NH_2$   (SEQ ID NO: 7), H—Gly—Trp—Thr—Leu—Asn—Ser—Ala—Gly—Tyr—Leu—Leu—Gly—Pro—Arg—His—Tyr—Ile—Asn—Leu—Ile—Thr—Arg—Gln—Arg—Tyr—$NH_2$   (SEQ ID NO: 8), H—Gly—Trp—Thr—Leu—Asn—Ser—Ala—Gly—Tyr—Leu—Leu—Gly—Ala—Arg—His—Tyr—Ile—Asn—Leu—Ile—Thr—Arg—Gln—Arg—Tyr—$NH_2$   (SEQ ID NO: 9), and H—Gly—Trp—Thr—Leu—Asn—Ser—Ala—Gly—Tyr—Leu—Leu—Gly—Pro—Pro—Pro—Tyr—Gly—Gly—Phe—Leu—$NH_2$   (SEQ ID NO: 10).

4. A pharmaceutical preparation comprising a galanin antagonist according to any one of claims 1, 2 or 3 as an active ingredient, together with pharmaceutically acceptable additive(s).

5. A method of treating a disorder in a mammal which depends on the physiological function of galanin at the galanin receptor, which comprises administering to said mammal a pharmacologically effective amount of a galanin antagonist according to any one of claims 1, 2 or 3.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 20
    ( D ) OTHER INFORMATION: /note="amide or free acid"

( x i ) SEQUENCE DESCRIPTION: SEQ ID NO:1:

Gly  Trp  Thr  Leu  Asn  Ser  Ala  Gly  Tyr  Leu  Leu  Gly  Pro  Gln  Gln  Phe
  1                   5                        10                       15

Phe  Gly  Leu  Met
                  20

( 2 ) INFORMATION FOR SEQ ID NO:2:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 21
    ( D ) OTHER INFORMATION: /note="amide or free acid"

( x i ) SEQUENCE DESCRIPTION: SEQ ID NO:2:

Gly  Trp  Thr  Leu  Asn  Ser  Ala  Gly  Tyr  Leu  Leu  Gly  Pro  Pro  Pro  Gly
  1                   5                        10                       15

Phe  Ser  Pro  Phe  Arg
                  20

( 2 ) INFORMATION FOR SEQ ID NO:3:

( i ) SEQUENCE CHARACTERISTICS:
    ( A ) LENGTH: 20 amino acids
    ( B ) TYPE: amino acid
    ( D ) TOPOLOGY: linear ( i i ) MOLECULE TYPE: peptide ( i i i ) HYPOTHETICAL: NO ( i x ) FEATURE:
    ( A ) NAME/KEY: Modified-site
    ( B ) LOCATION: 20
    ( D ) OTHER INFORMATION: /note="amide or free acid"

( x i ) SEQUENCE DESCRIPTION: SEQ ID NO:3:

Gly  Trp  Thr  Leu  Asn  Ser  Ala  Gly  Tyr  Leu  Leu  Gly  Pro  Pro  Pro  Leu

```
                  1               5                    10                  15
            Phe  Gly  Gly  Tyr
                              20
```

( 2 ) INFORMATION FOR SEQ ID NO:4:

( i ) SEQUENCE CHARACTERISTICS:
        ( A ) LENGTH: 21 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 21
        ( D ) OTHER INFORMATION: /note="amide or free acid"

( x i ) SEQUENCE DESCRIPTION: SEQ ID NO:4:

```
       Gly  Trp  Thr  Leu  Asn  Ser  Ala  Gly  Tyr  Leu  Leu  Gly  Pro  Pro  Pro  Gln
       1                   5                             10                       15
            Phe  Phe  Gly  Leu  Met
                              20
```

( 2 ) INFORMATION FOR SEQ ID NO:5:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 20
        ( D ) OTHER INFORMATION: /note="amide or free acid"

( x i ) SEQUENCE DESCRIPTION: SEQ ID NO:5:

```
       Gly  Trp  Thr  Leu  Asn  Ser  Ala  Gly  Tyr  Leu  Leu  Gly  Pro  Ala  Leu  Ala
       1                   5                             10                       15
            Leu  Ala  Leu  Ala
                              20
```

( 2 ) INFORMATION FOR SEQ ID NO:6:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 20
        ( D ) OTHER INFORMATION: /note="amide or free acid"

( x i ) SEQUENCE DESCRIPTION: SEQ ID NO:6:

```
       Gly  Trp  Thr  Leu  Asn  Ser  Ala  Gly  Tyr  Leu  Leu  Gly  Pro  Pro  Pro  Ala
       1                   5                             10                       15
            Leu  Ala  Leu  Ala
                              20
```

( 2 ) INFORMATION FOR SEQ ID NO:7:

( i ) SEQUENCE CHARACTERISTICS:
        ( A ) LENGTH: 20 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 20
        ( D ) OTHER INFORMATION: /note="amide or free acid"

( x i ) SEQUENCE DESCRIPTION: SEQ ID NO:7:

```
Gly Trp Thr Leu Asn Ser Ala Gly Tyr Leu Leu Gly Pro Pro Gly Phe
 1               5                  10                  15

Ser Pro Phe Arg
            20
```

( 2 ) INFORMATION FOR SEQ ID NO:8:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 25
        ( D ) OTHER INFORMATION: /note="amide or free acid"

( x i ) SEQUENCE DESCRIPTION: SEQ ID NO:8:

```
Gly Trp Thr Leu Asn Ser Ala Gly Tyr Leu Leu Gly Pro Arg His Tyr
 1               5                  10                  15

Ile Asn Leu Ile Thr Arg Gln Arg Tyr
            20                  25
```

( 2 ) INFORMATION FOR SEQ ID NO:9:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( i x ) FEATURE:
        ( A ) NAME/KEY: Modified-site
        ( B ) LOCATION: 25
        ( D ) OTHER INFORMATION: /note="amide or free acid"

( x i ) SEQUENCE DESCRIPTION: SEQ ID NO:9:

```
Gly Trp Thr Leu Asn Ser Ala Gly Tyr Leu Leu Gly Ala Arg His Tyr
 1               5                  10                  15

Ile Asn Leu Ile Thr Arg Gln Arg Tyr
            20                  25
```

( 2 ) INFORMATION FOR SEQ ID NO:10:

( i ) SEQUENCE CHARACTERISTICS:
        ( A ) LENGTH: 20 amino acids (B) TYPE: amino acid
(D) TOPOLOGY: linear (ii) MOLECULE TYPE: peptide (iii) HYPOTHETICAL: NO (ix) FEATURE:
(A) NAME/KEY: Modified-site
(B) LOCATION: 20
(D) OTHER INFORMATION: /note="amide or free acid"

(xi) SEQUENCE DESCRIPTION: SEQ ID NO:10:

```
Gly Trp Thr Leu Asn Ser Ala Gly Tyr Leu Leu Gly Pro Pro Pro Tyr
 1               5                  10                  15

Gly Gly Phe Leu
             20
```

(2) INFORMATION FOR SEQ ID NO:11:

(i) SEQUENCE CHARACTERISTICS:
(A) LENGTH: 22 amino acids
(B) TYPE: amino acid
(D) TOPOLOGY: linear (ii) MOLECULE TYPE: peptide (iii) HYPOTHETICAL: NO (ix) FEATURE:
(A) NAME/KEY: Modified-site
(B) LOCATION: 22
(D) OTHER INFORMATION: /note="amide"

(xi) SEQUENCE DESCRIPTION: SEQ ID NO:11:

```
Gly Trp Thr Leu Asn Ser Ala Gly Tyr Leu Leu Gly Pro Pro Pro Gln
 1               5                  10                  15

Gln Phe Phe Gly Leu Met
             20
```